United States Patent
Kleemiss

[11] Patent Number: 6,100,424
[45] Date of Patent: Aug. 8, 2000

[54] PROCESS FOR THE PREPARATION OF AMINO ACETIC ACID ESTERS WITH A TERTIARY HYDROCARBON RADICAL IN THE α-POSITION

[75] Inventor: Wolfgang Kleemiss, Haltern, Germany

[73] Assignee: Degussa-Huels Aktiengesellschaft, Frankfurt, Germany

[21] Appl. No.: 09/350,102

[22] Filed: Jul. 9, 1999

[30] Foreign Application Priority Data

Jul. 9, 1998 [DE] Germany ............... 198 30 632

[51] Int. Cl.⁷ .................. C07C 229/00; C07C 69/74
[52] U.S. Cl. .................. 560/155; 560/121; 560/123; 560/124; 560/125
[58] Field of Search .................. 560/155, 121, 560/123, 124, 125

[56] References Cited

U.S. PATENT DOCUMENTS 5,831,119 11/1998 Bauer et al. .

FOREIGN PATENT DOCUMENTS 0812822 4/1997 European Pat. Off. .

OTHER PUBLICATIONS

Miyazawa, T. et al "Synthesis of tert–Leucine" Konan Univ. Sci. Ser. No. 23 pp 51–54, 1979.
Streitwieser, A. et al "Introduction to Organic Chemistry" Macmillan: New York, p 801, 1976.

*Primary Examiner*—Gary Geist
*Assistant Examiner*—Leigh C. Maier
*Attorney, Agent, or Firm*—Oblon, Spivak, McClelland, Maier & Neustadt, P.C.

[57] ABSTRACT

Aminoacetic acid esters of formula I

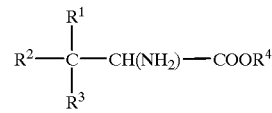

in which $R^1$, $R^2$ and $R^3$ are identical or different hydrocarbon radicals, or any two of these radicals form a carbon ring with the carbon atom to which they are attached and $R^4$ is hydrogen or an alkyl radical having 1–4 carbon atoms, are prepared by reacting an α-substituted malonic acid monoamide ester of formula II

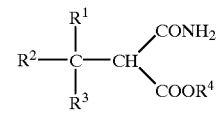

wherein $R^1$, $R^2$, $R^3$ and $R^4$ have the meanings above, by the Hofmann degradation reaction, with a hypohalite in an amount of up to 1.5 equivalents in an aqueous-basic medium containing base in an amount of 0.8–1.5 equivalents per mol. of starting malonic acid monoamide ester II.

12 Claims, No Drawings

PROCESS FOR THE PREPARATION OF AMINO ACETIC ACID ESTERS WITH A TERTIARY HYDROCARBON RADICAL IN THE α-POSITION

BACKGROUND OF THE INVENTION

Field of the Invention

The present invention relates to a process for the preparation of aminoacetic acid esters with a tertiary hydrocarbon radical in the α-position of formula I:

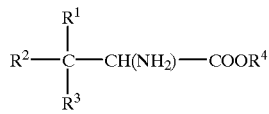

wherein $R^1$, $R^2$ and $R^3$ are identical or different hydrocarbon radicals, or any two of these radicals forming a carbon ring with the carbon atom on which they are a substituent, and $R^4$ is an alkyl radical having 1–4 carbon atoms, from the corresponding α-substituted malonic acid monoamide esters of formula II:

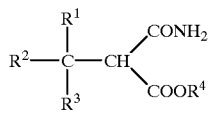

wherein $R^1$, $R^2$, $R^3$ and $R^4$ have the meanings above.

The simplest compounds I are the methyl or ethyl esters of α-tert-butylaminoacetic acid, which is also called tert-leucine ($R^1$, $R^2$ and $R^3$ methyl, $R^4$=methyl or ethyl).

DISCUSSION OF THE BACKGROUND

Amino acids and their esters are, inter alia, components for the preparation of proteins (see, for example, G. Krix, V. Eichhom, H. -O. Jakubke, M. -R. Kula, Enzyme Microb. Technol., 21 [1997], 252). Amino acids with a tertiary hydrocarbon radical in the α-position, such as tert-leucine and esters thereof, are of considerable importance as non-proteinogenic protein units which are useful for the synthesis of biologically active proteins having a particular action (A. S. Bommarius, M. Schwarm, K. Stingl, M. Kottenhahn, K. Huthmacher and K. Drauz, Tetrahedron: Asymmetry 6 [1995], 2851). tert-Leucine is furthermore useful as an auxiliary for asymmetric syntheses (U.Schöllkopf, Pure and Applied Chem. 55 [1983], 1799). The enantiomerically pure tert-leucine required for this purpose can be obtained by kinetic racemate cleavage of N-acyl tert-leucines with the aid of a specific deacylase (EP 0 494 716). tert-Leucine furthermore can easily be converted into tert-leucinol, which is used, for example, as a chiral auxiliary for the stereoselective synthesis of insecticides (M. J. McKennon, A. I. Meyers, K. Drauz and M. Schwarn, J. Org. Chem. 58 [1993], 3568). It should be possible to use aminoacetic acids with other tertiary hydrocarbon radicals, e.g. higher homologues of tert-leucine, in a corresponding manner. tert-Leucine can be prepared by the Strecker synthesis from pivalaldehyde (K. Ogura, Bull. Chem. Soc. Jpn. 65 [1992], 2359) or by ammonolysis of 2-bromo-3,3-dimethylbutyric acid (E. Abderhaiden, Z. Phys. Chem. 228 [1934], 193). Aminoacetic acids with other tertiary hydrocarbon radicals in the α-position can be prepared in a corresponding manner from other corresponding aldehydes by the Strecker synthesis or from other corresponding bromocarboxylic acids by ammonolysis. Another known process for preparation of tert-leucine is the enzyme-catalyzed transamination of 3,3-dimethyl-2-oxobutyric acid (EP 0 248 357).

Both pivalaldehyde and 2-bromo-3,3-dimethylbutyric acid and 3,3-dimethyl-2-oxobutyric acid are relatively expensive starting substances. Other aldehydes and other bromocarboxylic acids are also expensive, from which aminoacetic acids having other tertiary hydrocarbon radicals in the α-position can be prepared. Furthermore, hydrocyanic acid, which requires significant safety precautions, is required for the Strecker synthesis. In the enzyme-catalyzed transamination mentioned above, the space/time yields are unsatisfactory.

The enantioselective synthesis of (R)-tert-leucine has also been described. In the process, N-carbamoyl-(R)-tert-leucine, which can be converted into (R)-tert-leucine, for example, with a (R)-carbamoylase, is prepared from tert-butylhydantoin with the aid of a (R)-specific hydantoinase (DE 19529211). (R)-tert-Leucine is obtained in a yield of 85.5%, based on the tert-butyl-hydantoin employed, but no information on the enantiomer purity is described in the patent specification. Furthermore, the cleavage of N-carbamoyl-(R)-tert-leucine by means of nitrite is described in the patent specification. The reaction time here is long, and furthermore an aqueous reaction mixture of high salt content, which must be purified in an expensive manner by ion exchange chromatography, is obtained.

Another patent application (DE 19724086) describes the preparation of aminoacetic acids with a tertiary hydrocarbon radical in the α-position by Hofmann degradation of malonic acid monoamide esters with a tertiary hydrocarbon radical in the α-position. In this process, not only is the carboxamide group degraded to the amino group, but the carboxylic ester group is also hydrolyzed to the carboxyl group. The stereoselective synthesis of (R)-tert-leucine from (S)-tert-butylmalonic acid monoamide ester by Hofmann degradation is also described in the patent application. In this process, 1.5–4 equivalents of sodium hydroxide solution and 1–1.2 equivalents of sodium hypochlorite solution are employed. The aminoacetic acid is obtained in a yield of 85%. In this case also, after neutralization of the reaction mixture with hydrochloric acid, the aminoacetic acid is obtained as a coupled product together with large amounts of sodium chloride, and this product in turn is separated by means of ion exchangers.

SUMMARY OF THE INVENTION

Accordingly, one object of the invention is to provide a process by which esters of aminoacetic acids, having a tertiary hydrocarbon radical in the α-position, can be prepared in good yields and space/time yields and without using starting materials which require safe handling precautions and without expensive separation or purification, starting from inexpensive starting substances.

Briefly, this object and other objects of the invention as hereinafter will become more readily apparent can be attained in a process for the preparation of aminoacetic acid esters, having a tertiary hydrocarbon radical in the α-position, of formula I:

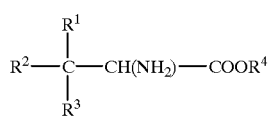

wherein $R^1$, $R^2$ and $R^3$ are identical or different hydrocarbon radicals, or any two of the radicals form a carbon ring with the carbon atom to which they are attached, and $R^4$ is an alkyl radical having 1–4 carbon atoms, comprising:

reacting an α-substituted malonic acid monoamide ester of formula II:

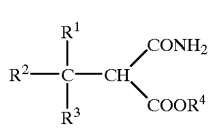

wherein $R^1$, $R^2$, $R^3$ and $R^4$ have the meanings above, by the Hofmann degradation reaction, with a hypohalite in an amount of up to 1.5 equivalents in an aqueous-basic medium containing base in an amount of 0.8–1.5 equivalents per mol. of starting malonic acid monoamide ester II.

DESCRIPTION OF THE PREFERRED EMBODIMENTS

The esters of the amino acids with a tertiary hydrocarbon radical in the α-position are obtained in high yields in spite of the comparatively low excess of base. This is surprising, since the Hofmann degradation is usually conducted with at least two equivalents of base per equivalent of carboxamide group in order to achieve high yields (Organic Reactions III [1946], 2679). It is furthermore surprising that the carboxylic ester group is practically not attacked under the conditions of the Hofmann degradation, although carboxylic acid esters are usually smoothly hydrolyzed with dilute alkalis at a relatively high temperature to give the carboxylic acid salts (see, for example, J. March, Advanced Organic Chemistry-Reactions, Mechanisms and Structure, 3rd Edition [1985], 334). This is evidently to be attributed to the tertiary hydrocarbon radical. In contrast to, for example, α-tert-butylmalonic acid monoamide methyl or ethyl ester, the corresponding n-butyl-substituted isomer, which can be employed in a manner not within the scope of the invention, results in considerable amounts of the corresponding free acid or salt thereof. The virtual non-hydrolyzability of the carboxylic ester group is of particular advantage, because reaction product I separates from the aqueous reaction mixture as a separate organic phase. Expensive separation operations by means of ion exchangers are thus not necessary. If the esters are subjected to controlled acid hydrolysis, the amino acids are indeed obtained as a mixture with salts. However, the amount of salt is considerably smaller than in the process of The starting materials II can be prepared in a known manner with high overall yields from the corresponding tert-alkylmalonic acid dialkyl esters, which are initially partly hydrolyzed to the monoesters. The monoesters are converted into the carboxylic acid halide, which gives the monoamide II with ammonia by reaction with ammonia (G. S. Bajwa, S. Chandrasekaran, J. H. Hargis, A. E. Sopchik, D. Blatter, W. G. Bentrude, J. Am. Chem. Soc. 104 [1982], 6385). German patent application P 19623142.6 describes the synthesis of enantiomerically enriched tert-alkylmalonic acid monoesters. These monoesters can be converted into the corresponding enantiomerically enriched starting materials II in the manner described. In preferred starting materials II (and, therefore, also in the products 1), $R^1$, $R^2$ and $R^3$ are an alkyl radical having 1–4 carbon atoms or a benzyl or phenylethyl radical, or two of these substituents, with the carbon atom on which they are a substituent, form a cycloalkyl ring having 5–8 ring members. $R^4$ is preferably methyl or ethyl.

Alternatively, the starting materials II can be prepared from the corresponding tert-alkylmalonic acid mononitriles by hydrolysis of the nitrile function to the carboxamide function (Perez-Ossorio, Alemany, An. Soc. Espan. [B] 54, 471 [1958]) and subsequent esterification of the malonomonocarboxamide acid.

Suitable starting materials II include, for example, α-tert-butylmalonic acid monoamide methyl ester, α-tert-butylmalonic acid monoamide ethyl ester, α-tert-pentylmalonic acid monoamide ethyl ester, α-(1-methyl-1-phenylethyl)-malonic acid monoamide ethyl ester, α-[1'-methylcyclohex-1'-yl]-malonic acidmonoamide ethyl ester, α-[2-ethylbut-2-yl]-malonic acid monoamide ethyl ester and α-[2-benzylprop-2-yl]-malonic acid monoamide ethyl ester.

A base and hypohalite, i.e. a salt of a hypohalous acid, are required for the Hofmann degradation reaction. Of the hypohalite solutions, the readily accessible, inexpensive hypochlorites are expediently employed. The preferred hypochlorites are potassium hypochlorite and, in particular, sodium hypochlorite in the form of an aqueous solution, which is also called bleaching liquor. Calcium hypochlorite can also be used, but gives lower yields. It is an essential feature of the invention that the hypohalite is used in the above-mentioned amounts. It is preferably used in an amount of 1.0–1.2 equivalents, based on the starting material II.

Preferred bases are the alkali metal hydroxides, such as potassium hydroxide, and in particular sodium hydroxide, again in the form of their aqueous solutions. Alkaline earth metal hydroxides are also suitable but give lower yields. In general, a base with the cation which is also present in the hypohalite is used. The abovementioned amount of base is critical and decisive for the success of the process. The base is preferably employed in an amount of 0.9–1.2 equivalents per equivalent of the starting material II.

The reaction takes place in an aqueous basic medium. In general, 50–95, in particular 60–90% by weight of the reaction mixture is water.

The process of the invention can be conducted continuously or discontinuously. In a discontinuous embodiment with sodium hydroxide as the base and sodium hypochlorite as the salt of a hypohalous acid, the starting material II is initially introduced at a temperature which is normally 0–20° C., preferably 5–10° C., into an approximately 10–15 percent strength by weight sodium hypochlorite solution. The mixture is stirred at this temperature for about 1–5 hours, preferably 2–3 hours, the sodium hydroxide is then added to the reaction mixture as a 5–50 percent strength aqueous sodium hydroxide solution and the mixture is heated to a temperature of 40–100° C., preferably 60–80° C. The reaction is finished in 2 minutes to 3 hours, preferably after 5 minutes to 2 hours, depending on the temperature.

After cooling of the reaction mixture, the product I is separated as the upper organic phase. The aqueous lower phase can be extracted with the aid of an inert organic solvent to obtain further product. After drying, organic solvent can be removed from the combined organic phases. A crude ester is thus obtained, and can be purified by distillation and/or acid extraction with subsequent alkalinization of the acid extract and extraction with an inert organic solvent. The ester of the corresponding aminoacetic acid is obtained in this way with a purity, determined by gas chromatography, of >98% in a yield of about 80%.

If an enantiomerically enriched starting material II is reacted as described, an enantiomerically enriched aminoacetic acid ester I is obtained in the same yield and purity, the enantiomer purity of the starting material being obtained.

The reaction can also be carried out in the presence of an inert organic solvent. If the organic solvent is not miscible with the aqueous reaction medium, the aminoacetic acid ester formed is separated from the reaction medium by extraction. Suitable solvents include, for example, alcohols, for example, having 1–10, preferably 1–4 carbon atoms, such as methanol, ethanol and isopropanol; ethers, for example, having 4–10, preferably 4–6 carbon atoms, such as diethyl ether and methyl tert-butyl ether; and hydrocarbons, preferably having 5–10 carbon atoms, such as toluene, cyclohexane and aliphatic hydrocarbons having boiling points ranging from 50–100° C.

The process of the invention can also be conducted continuously, for example, by a procedure analogous to that described in EP 0 676 390. In the continuous process a mixture of compounds of starting material II is brought into contact continuously with an alkali metal hypohalite solution at 0–20° C., preferably at 5–10° C., for a sufficiently long time. The solution of an alkali metal hydroxide or alkaline earth metal hydroxide is then added to the reaction mixture and the reaction mixture is heated at a temperature of 50–10° C. for 2 minutes to one hour, preferably 2–30 minutes. When the reaction has ended, the reaction mixture is worked up continuously or batchwise, as described. Continuous work-up of the reaction mixture includes continuous separation of the aminoacetic acid ester formed.

The crude or purified aminoacetic acid ester I can be converted into the free aminoacetic acid I, for example, by acid hydrolysis, as has been described, for example, by D. A. Jaeger, M. D. Broadhurst, D. J. Cram in J. Am. Chem. Soc. 101 (1979), 717. The protective action of the tertiary hydrocarbon radical is evidently not sufficient to protect the carboxylic ester group from acid hydrolysis.

Having now generally described the invention, a further understanding can be obtained by reference to certain specific examples which are provided herein for purpose of illustration only and are not intended to be limiting unless otherwise specified.

EXAMPLES

Example 1

A 10 g (0.053 mol.) amount of tert-butylmalonic acid monoethyl ester amide is stirred in 36.9 g (0.058 mol.) of aqueous 11.7 percent strength by weight sodium hypochlorite solution and 10 g of water at 0–5° C. in a stirred vessel. After 3 hours, the solid has dissolved completely. 10.6 g (0.053 mol.) of 20 percent strength by weight sodium hydroxide solution are then added in the cold and the reaction mixture is heated rapidly at 80° C. for 2.5 minutes. During this operation, the reaction temperature rises to 103° C. The reaction mixture is allowed to cool to room temperature and the organic phase is separated. The aqueous phase is extracted twice with 100 ml of methyl tert-butyl ether each time. The combined organic phases are dried over sodium sulfate and the solvent is removed. With dioxane as the internal standard, a yield, determined by gas chromatography, of 2-tert-butyl-aminoacetic acid ethyl ester (tert-leucine ethyl ester) of 6.32 g (75%) results.

Example 2

A 10 g (0.053 mol.) amount of tert-butylmalonic acid monoethyl ester amide is stirred in 36.9 g (0.058 mol.) of aqueous 11.7 percent strength by weight sodium hypochlorite solution and 10 g of water at 0–5° C. in a stirred vessel. After 3 hours, the solid has dissolved completely. 10.6 g (0.053 mol.) of 20 percent strength by weight sodium hydroxide solution are then added in the cold and the reaction mixture is heated rapidly at 80° C. for 2.5 minutes. During this operation, the reaction temperature rises to 104° C. The reaction mixture is allowed to cool to room temperature and the organic phase is separated. The aqueous phase is extracted twice with 50 ml of methyl tert-butyl ether each time. The combined organic phases are extracted several times with 5 percent strength by weight hydrochloric acid. Thereafter, the combined acid extracts are rendered alkaline with dilute sodium hydroxide solution and extracted again with methyl tert-butyl ether. The organic phase is dried over sodium sulfate and the solvent is removed 6.2 g (74%) of tert-leucine ethyl ester with a purity, determined by GC, of >98% are obtained.

Example 3

A 30 g (0.16 mol.) amount of tert-butylmalonic acid monoethyl ester amide is stirred in 110.7 g (0.174 mol.) of aqueous 11.7 percent strength by weight sodium hypochlorite solution and 30 g of water at 0–5° C. in a stirred vessel. After 3 hours, the solid has dissolved completely. 31.8 g (0.16 mol.) of 20 percent strength by weight sodium hydroxide solution are then added in the cold and the reaction mixture is heated rapidly at 80° C. for 2.5 minutes. During this operation, the reaction temperature rises to 105° C. The reaction mixture is allowed to cool to room temperature and the organic phase is separated. The aqueous phase is extracted twice with 100 ml of methyl tert-butyl ether each time. The combined organic phases are dried over sodium sulfate and the solvent is removed. The residue is distilled in vacuo. Under a pressure of 6 mbar at an overhead temperature of 75° C., a main fraction of 18.5 g is obtained. According to GC, this fraction comprises >98% tert-leucine ethyl ester. The yield upon distillation is, therefore, 79%.

Example 4

A 10 g (0.053 mol.) of tert-butylmalonic acid monoethyl ester amide with an enantiomer excess of 86% is stirred in 36.9 g (0.058 mol.) of aqueous 11.7 percent strength by weight sodium hypochlorite solution and 10 g of water at 0–5° C. in a stirred vessel. After 4 hours, the solid has dissolved completely. 10.6 g (0.053 mol.) of 20 percent strength by weight sodium -hydroxide solution are then added in the cold and the reaction mixture is heated rapidly at 80° C. for 3 minutes. During this operation, the reaction temperature rises to 100° C. The reaction mixture is allowed to cool to room temperature and is extracted three times with 50 ml of methyl tert-butyl ether each time. The combined organic phases are dried over sodium sulfate and the solvent is removed. With dioxane as the internal standard, a yield, determined by gas chromatography, of tert-butylaminoacetic acid ester of 5.93 g (70%) results.

In order to determine the enantiomer excess, the reaction product is extracted with dilute hydrochloric acid. The acid aqueous phase is rendered alkaline with dilute sodium hydroxide solution and the ethyl ester of tert-leucine is extracted with methyl tert-butyl ether. The organic phase is dried over sodium sulfate and the solvent is removed. The residue is heated under reflux with 20 g of formic acid for 2 hours.

After removal of the formic acid by distillation, N-formyl-tert-leucine ethyl ester remains. Analysis with the aid of a chiral GC column gives an enantiomer excess of the (R)-tert-leucine ethyl ester of 84%.

Example 5

Comparison Example

A 5 g (0.026 mol.) amount of n-butylmalonic acid monoethyl ester amide is stirred in 16.27 g (0.028 mol.) of aqueous 13 percent strength by weight sodium hypochlorite solution and 10 g of water at 0–5° C. in a stirred vessel for 3 hours. Thereafter, the solid has dissolved completely. 5.2 g (0.026 mol.) of 20 percent strength by weight sodium hydroxide solution are then added in the cold and the reaction mixture is heated rapidly at 80° C. for 2.5 minutes. During this operation, the reaction temperature rises to 84° C. The reaction mixture is allowed to cool to room temperature and is extracted three times with 100 ml of methyl tert-butyl ether each time. The combined organic phases are dried over sodium sulfate and the solvent is removed. Only about 0.2 g of organic material, which comprises no 2-aminobutyric acid ethyl ester, remains as the residue. The 2-aminobutyric acid formed in the reaction remains as the sodium salt in the aqueous phase. The ethyl ester, therefore, cannot be prepared in this manner.

The disclosure of German priority application Serial No. 19830632.6 filed Jul. 9, 1998 is hereby incorporated by reference into the application.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent:

1. A process for preparing aminoacetic acid esters, having a tertiary hydrocarbon radical in the α-position, of formula I

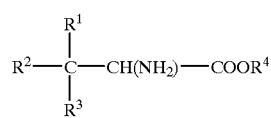

wherein $R^1$, $R^2$ and $R^3$ are identical or different hydrocarbon radicals, or any two of the radicals form a carbon ring with the carbon atom to which they are attached, and $R^4$ is an alkyl radical having 1–4 carbon atoms, comprising:

reacting an α-substituted malonic acid monoamide ester of formula II

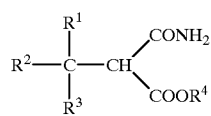

wherein $R^1$, $R^2$, $R^3$ and $R^4$ have the meanings above with a hypohalite in an amount of 1.0–1.5 equivalents in an aqueous-basic medium containing base in an amount of 0.8–1.5 equivalents per mol. of starting malonic acid monoamide ester II.

2. The process as claimed in claim 1, wherein the amount of hypohalite ranges from 1.0–1.2 equivalents and the amount of base ranges from 0.9–1.2 equivalents per mol. of starting malonic acid monoamide ester II.

3. The process as claimed in claim 1, wherein said hypohalite is an alkali metal hypochlorite and an alkali metal hydroxide is the base.

4. The process as claimed in claim 3, wherein the alkali metal hypochlorite is sodium hypochlorite and the alkali metal hydroxide is sodium hydroxide.

5. The process as claimed in one of claim 1, wherein the process is conducted discontinuously by first allowing a hypochlorite solution to act on the starting material II at 0–20° C. for 1–5 hours, then adding the base, increasing the temperature to 40–100° C., continuing the reaction for 1–5 hours and separating the aminoacetic acid ester I formed from the reaction mixture, as an upper, organic phase.

6. The process as claimed in claim 1, wherein the process is conducted continuously by bringing a compound of starting material II into contact with an alkali metal hypohalite solution continuously at 0–20° C. for a sufficiently long time, adding the solution of an alkali metal hydroxide or alkaline earth metal hydroxide to the reaction mixture, heating the reaction mixture at a temperature of 50–100° C. for 2 minutes to 1 hour and, when the reaction has ended, working-up the mixture continuously to continuously separate the aminoacetic acid ester I formed.

7. The process as claimed in claim 1, wherein the reaction is conducted in the presence of an inert organic solvent.

8. The process as claimed in claim 7, wherein the solvent is an alcohol, an ether or a hydrocarbon.

9. The process as claimed in claim 1, wherein said α-substituted malonic acid monoamide ester of formula II is α-tert-butylmalonic acid monoamide methyl ester, α-tert-butylmalonic acid monoamide ethyl ester, α-tert-pentylmalonic acid monoamide ethyl ester, α-(1-methyl-1-phenylethyl)-malonic acid monoamide ethyl ester, α-[1'-methylcyclohex-1'-yl]-malonic acid monoamide ethyl ester, α-[2-ethylbut-2-yl]-malonic acid monoamide ethyl ester or α-[2-benzylprop-2-yl]-malonic acid monoamide ethyl ester.

10. The process as claimed in claim 7, wherein the inert organic solvent is a $C_{1-10}$-alcohol, an ether having a carbon atom content of 4–10 or a $C_{5-10}$-hydrocarbon.

11. The process as claimed in claim 10, wherein the organic solvent is methanol, ethanol, isopropanol, diethyl ether, methyl t-butyl ether, toluene or cyclohexane.

12. The process as claimed in claim 1, wherein $R^1$, $R^2$ and $R^3$ are each a $C_{1-4}$-alkyl radical, benzyl or phenylethyl group, or any two of these substituents, with the carbon atom on which they are attached form a $C_{5-8}$-cycloalkyl group and $R^4$ is methyl or ethyl.

* * * * *